(12) United States Patent
DiBattiste et al.

(10) Patent No.: US 6,770,660 B2
(45) Date of Patent: Aug. 3, 2004

(54) METHOD FOR INHIBITING PLATELET AGGREGATION

(75) Inventors: Peter M. DiBattiste, Chalfont, PA (US); David Schneider, Shelburne, VT (US)

(73) Assignee: Artery LLC, Baltimore, MA (US)

( * ) Notice: Subject to any disclaimer, the term of this patent is extended or adjusted under 35 U.S.C. 154(b) by 0 days.

(21) Appl. No.: 10/427,436

(22) Filed: May 1, 2003

(65) Prior Publication Data

US 2003/0207918 A1 Nov. 6, 2003

Related U.S. Application Data

(60) Provisional application No. 60/380,084, filed on May 6, 2002.

(51) Int. Cl.$^7$ .......................................... A61K 31/445
(52) U.S. Cl. ........................................ 514/331
(58) Field of Search ........................................ 514/331

(56) References Cited

U.S. PATENT DOCUMENTS

| | | | |
|---|---|---|---|
| 4,492,753 A | | 1/1985 | Shell et al. |
| 5,292,756 A | * | 3/1994 | Duggan et al. ............. 514/331 |
| 5,763,427 A | | 6/1998 | Weitz et al. |

FOREIGN PATENT DOCUMENTS

| | | |
|---|---|---|
| WO | WO 97/35579 | 10/1997 |
| WO | WO 97/35592 | 10/1997 |
| WO | WO 99/38827 | 8/1999 |

OTHER PUBLICATIONS

Neumann et al, J. Am. Coll. Cardiol., vol. 37, pp. 1323–1328 (2001).*
Topol et al, N. Engl. J. Med., vol. 344, pp. 1888–1894 (2001).*
Kabbani et al, The Am. J. Cardiol., vol. 89, pp. 647–650, (2002).*
Lynch et al, J. Pharmacol. Exp. Ther., vol. 272(1), pp. 20–32 (Jan. 1995).*
Circulation, vol. 96(5), pp. 1445–1453 (abstract) (Sep. 1997).*
Gibson et al, J. Am. Coll. Cardiol., vol. 32(1) pp. 28–34 (abstract) (Jul. 1998).*
McClellan et al, Drugs, vol. 56(6), pp. 1067–1080 (abstract) (Dec. 1998).*
Dagdelen et al, Int. Angiol., vol. 20(3), pp. 244–247 (abstract) (Sep. 2001).*
Leo G. Frederick, et al., Circulation, vol. 93, No. 1, Jan. 1, 1996.
Dean J. Kereiakes, Circulation, vol. 94, No. 5, Sep. 1, 1996.
Clive Kearon, The New England Journal of Medicine, vol. 338, No. 2, Jan. 8, 1998.
Karsten Schror, Drugs, vol. 50, No. 1, Jul. 1995, pp. 1–196.
Nigel S. Cook, Drugs of the Future, 1994, 19(2): pp. 135–159.
J. Lefkovits, European Heart Journal, 1996, 17, 9–1.
Marc Cohen, The New England Journal of Medicine, vol. 337, No. 7, Aug. 14, 1997.
Charles Landau, The New England Journal of Medicine, vol. 330, No. 14, Apr. 7, 1994.

* cited by examiner

*Primary Examiner*—Raymond J. Henley, III
(74) *Attorney, Agent, or Firm*—Paul W. Kletzly; Hansjorg Sauer

(57) ABSTRACT

A method for inhibiting platelet aggregation in a patient in need thereof, comprising 1) administering to the patient a bolus injection of an active drug, in an amount of about 25 $\mu$g/kg, and 2) administering to the patient, after the bolus injection, an intravenous infusion for a period of between about 12 hours and about 72 hours, of the active drug, in an amount of about 0.15 $\mu$g/kg/min, wherein the active drug is tirofiban or a salt thereof.

6 Claims, No Drawings

METHOD FOR INHIBITING PLATELET AGGREGATION

This application claims benefit of U.S. Provisional Application Serial No. 60/380,084 filed May 6, 2002.

BACKGROUND OF THE INVENTION

Platelet activation and aggregation are involved in unstable angina and acute myocardial infarction, in reocclusion following thrombolytic therapy and angioplasty, in transient ischemic attacks, and in a variety of other vasoocclusive disorders. When a blood vessel is damaged, either by acute intervention such as angioplasty, or, more chronically, by the pathophysiological processes of atherosclerosis, platelets are activated to adhere to the disrupted surface and to each other. This activation, adherence and aggregation may lead to occlusive thrombus formation in the lumen of the blood vessel.

Antiplatelet therapy has been used in a wide variety of cardiovascular disease states and in conjunction with interventional therapy such as coronary artery or peripheral bypass grafting, cardiac valve replacement, and percutaneous transluminal coronary angioplasty. Inhibitors of the glycoprotein complex GP IIb/IIIa, including abciximab, tirofiban, and eptifibatide, are used intravenously to inhibit platelet aggregation. Platelet aggregation inhibition results in reduced incidences or reduced severity of adverse events such as death or damage to the heart. Typical use of these inhibitors involves initial bolus injection and subsequent sustained infusion, for a period of hours or days.

Holmes et al., Coronary Artery Disease (2001) 12:245–253, describe the efficacy of platelet aggregation inhibition induced by treatment with tirofiban hydrochloride in patients with unstable angina, non-ST-segment elevation myocardial infarction or symtomatic coronary disease undergoing percutaneous coronary intervention. Patients received either 0.4 µg/kg/min over 30 minutes followed by 0.1 µg/kg/min, or 10 µg/kg bolus injection followed by continuous infusion at 0.15 µg/kg/min.

Neumann, et al., J. Am. Coll. Cardiol. (2001) vol. 37, pp. 1323–1328, describe antiplatelet effects if tirofiban hydrochloride in patients undergoing intracoronary stent placement for symptomatic coronary artery disease. Patients received 10 µg/kg bolus injection followed by continuous infusion at 0.15 µg/kg/min for 72 hours.

Topol et al., N Engl J Med, (2001) vol. 344, pp. 1888–1894, describe the use of tirofiban hydrochloride for the prevention of ischemic events with percutaneous coronary revascularization. Treated patients were those scheduled to undergo a coronary stenting procedure of a newly stenotic or restenotic atherosclerotic lesion in a native vessel or a bypass graft. Patients received 10 µg/kg bolus injection followed by continuous infusion at 0.15 µg/kg/min for 18–24 hours.

Kabbani et al. The American Journal of Cardiology (2002) vol. 89 pp. 647–650, describe the use of tirofiban hydrochloride in patients having an acute coronary syndrome in whom a percutaneous coronary intervention was mandated. Patients received 10 µg/kg bolus injection followed by continuous infusion at 0.15 µg/kg/min for 18–24 hours. Results from the study show that the average inhibition of maximal aggregation during the period of time between 15 and 60 minutes following administration of the bolus dose was between 61% and 66%.

In each of the above studies, patients were treated either with no bolus dose of tirofiban hydrochloride or a 10 µg/kg bolus dose of tirofiban. The duration of continuous infusion was between 18 and 72 hours. In no case was the bolus amount greater than 10 µg/kg.

We have now found that substantially more effective inhibition of platelet aggregation can be obtained by administering, to a patient in need thereof, a bolus dose of tirofiban hydrochloride of about 25 µg/kg. The increased bolus dose greatly improves the overall platelet aggregation inhibitory effect of tirofiban therapy, providing an aggregation inhibition of greater than 90%, without the need to increase the concentration of tirofiban hydrochloride solution delivered during the continuous infusion phase of tirofiban therapy, and without the need to extend the duration of the continuous infusion phase. Further, this benefit is achieved in the absence of increased undesirable side effects.

SUMMARY OF THE INVENTION

The invention is a method for inhibiting platelet aggregation in a patient in need thereof, comprising 1) administering to the patient a bolus injection of an active drug, in an amount of about 25 µg/kg, and 2) administering to the patient, after the bolus injection, an intravenous infusion of an active drug for a period of between about 12 hours and about 72 hours, in an amount of about 0.15 µg/kg/min, wherein the active drug is tirofiban or a salt thereof.

In a class of methods of the invention, the salt is tirofiban hydrochloride. In a subclass of the class, the amount of tirofiban hydrochloride in the bolus injection is 25 µg/kg. In another subclass of the class, the intravenous infusion is between 12 hours and 72 hours, e.g. between 18 hours and 72 hours.

The invention is also a method for reducing the risk of acute coronary syndrome in a patient at risk to acute coronary syndrome, comprising 1) administering to the patient a bolus injection of an active drug, in an amount of between about 25 µg/kg, and 2) administering to the patient, after the bolus injection, an intravenous infusion for a period of between about 12 hours and about 72 hours, of the active drug, in an amount of about 0.15 µg/kg/min, wherein the active drug is tirofiban or a salt thereof.

DETAILED DESCRIPTION OF THE INVENTION

Tirofiban hydrochloride, commercially available as AGGRASTAT®, is a non-peptide antagonist for the glycoprotein IIb/IIIa fibrinogen receptor. Tirofiban hydrochloride is chemically described as N-(butylsulfonyl)-O-[4-(4-piperidinyl)butyl]-L-tyrosine monohydrochloride and structurally represented as

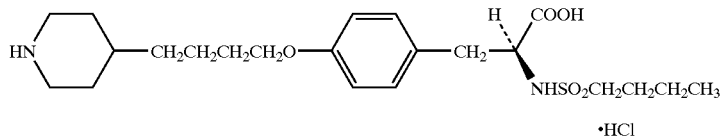

•HCl

Tirofiban hydrochloride is also referred to as (2-S-(n-Butylsulfonylamino)-3[4-(piperidin-4-yl)butyloxyphenyl] propionic acid hydrochloride, and is described in U.S. Pat. No. 5,292,756.

Tirofiban hydrochloride and related pharmaceutically acceptable salts are useful in the present invention. The term "pharmaceutically acceptable salts" means non-toxic salts of the compounds which include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

Tirofiban, tirofiban hydrochloride, and other tirofiban salts, are also collectively referred to hereinafter as "active drug."

Pharmaceutically effective amounts of the active drug are suitable for use in the methods of the present invention. The term "pharmaceutically effective amount" means that amount of a drug or pharmaceutical agent that will elicit the biological or medical response of a tissue, system or animal that is being sought by a researcher or clinician.

The methods of the present invention are useful in combination with other procedures for treating candidate patients, including procedures involving treatments with other anticoagulants (e.g. heparin and warfarin), thrombolytic agents (e.g. streptokinase and tissue plasminogen activator), and platelet antiaggregation agents (e.g. aspirin and dipyridamole).

The dosage regimen utilizing the active drug is selected in accordance with weight of the patient; an ordinarily skilled physician or veterinarian can readily determine and prescribe the effective amount of the drug required to prevent, counter, or arrest the progress of the condition in accordance with the present invention.

The active drug can be administered in admixture with suitable pharmaceutical diluents, excipients or carriers (collectively referred to herein as "carrier" materials) suitably selected with respect to the intended form of administration and consistent with conventional pharmaceutical practices.

The methods according to the present invention for administering the active drug are useful for treating patients where inhibition of human or mammalian platelet aggregation or adhesion is desired. They are useful in surgery on peripheral arteries (arterial grafts, carotid endaterectomy) and in cardiovascular surgery where manipulation of arteries and organs, and/or the interaction of platelets with artificial surfaces, leads to platelet aggregation and potential formation of thrombi and thromboemboli. Methods of the invention may be used to prevent the formation of thrombi and thromboemboli. Other applications include prevention of platelet thrombosis, thromboembolism and reocclusion during and after thrombolytic therapy and prevention of platelet thrombosis, thromboembolism and reocclusion after angioplasty or coronary artery bypass procedures. The methods may also be used to prevent myocardial infarction.

The present invention is demonstrated in a study of patients with acute coronary syndrome who are undergoing early coronary revascularization with percutaneous coronary angioplasty or atherectomy. Because of unstable plaque with thrombus, percutaneous revascularization procedures in these patients carry with them considerable higher morbidity than procedures performed in patients with stable coronary disease. Patients are evaluated after treatment for acute coronary syndrome and may require follow-up intervention associated with acute coronary syndrome, including coronary artery bypass grafting, repeat percutaneous intervention for acute ischemia, and insertion of a coronary endovascular stent.

EXAMPLE 1

Treatment of Acute Coronary Syndrome

Eligible patients included those with an acute coronary syndrome in whom a percutaneous coronary intervention was clinically mandated. An acute coronary syndrome was defined by the following criteria; ischemic symptoms plus either 0.5 mm of ST segment depression on the ECG or an elevated troponin or creatine kinase MB fraction. Exclusion criteria included treatment with an antiplatelet agent other than aspirin in the previous 14 days, thrombolytic therapy within 24 hours, renal insufficiency (creatinine greater than 2.5 mg/dl), and any contraindication to treatment with a glycoprotein IIb-IIIa inhibitor.

Patients were treated with a 20 μg/kg bolus of tirofiban hydrochloride followed by a 0.15 μg/kg/min infusion for 18–24 hours or a 25 μg/kg bolus followed by the same infusion. Enrollment of subjects in the panel with the 20 μg/kg bolus (n=15/panel) was completed and the clinical effects and pharmacodynamic properties were evaluated before subjects were enrolled in the panel with the 25 μg/kg bolus. Patients were treated with aspirin (325 mg before the procedure and daily) and unfractionated heparin (target activated clotting time 250 seconds). Clopidogrel (300 mg and then 75 mg daily)(commercially available as PLAVIX®) was administered at least 45 minutes after the start of tirofiban hydrochloride. All other medications were administered at the discretion of the attending cardiologist. Sheath removal was performed when the activated clotting time was less than 175 seconds unless a closure device was used.

Blood samples were obtained from a venous catheter for assessment of platelet function by light transmission aggregometry, rapid platelet function analyzer and flow cytometry before treatment and after 15, 30, 45, and 60 minutes. Blood was obtained after 5 minutes for analysis by flow cytometry. Blood for light transmission aggregometry and rapid platelet function analyzer was anticoagulated with D-Phe-Pro-Arg-chloromethyl ketone (38 μM) to avoid potentially confounding effects of citrate on inhibitory properties of tirofiban hydrochloride (Rebello et al., J. Thromb. Thrombolysis (2000) vol. 9 pp. 23–28). Blood for flow cytometry was anticoagulated with corn trypsin inhibitor, a specific inhibitor of coagulation factor XIIa without effect on other coagulation factors (Schneider et al., Circulation (1997) vol. 96 pp. 2877–83). Aggregation (light transmission aggregometry) of platelets was assessed in platelet rich plasma in response to 20 µM adenosine diphosphate (Chronolog). Maximal aggregation (ex vivo) after 4 minutes was determined. rapid platelet function analyzer was performed in accordance with manufacturer specifications with thrombin receptor agonist peptide cartridges. Assessment of the capacity of platelets to bind fibrinogen was performed as previously described (Holmes et al., Coron. Artery Dis. (2001) vol. 12 pp. 245–253; Kabbani et al., Circulation (2001) vol. 104 pp. 181–186). For flow cytometry, samples were processed and platelets were fixed at each site.

The study was designed to identify a bolus dose of tirofiban hydrochloride that inhibited platelet aggregation, on average, by at least 90% with a lower 95% confidence interval of the extent of inhibition of at least 85% at all times between 15 to 60 minutes after onset of treatment. The occurrence of 3 major bleeding episodes (as defined by the American College of Cardiology Task force (Cannon et al. J. Am. Coll. Cardiol. (2001) vol. 38 pp. 2114–30) in each panel was a pre-specified criteria for termination of the study.

The activated clotting time at the time of percutaneous coronary intervention was 249±24 seconds. No major bleeding episode occurred with either the 20 µg/kg or 25 µg/kg bolus.

The average extent of inhibition of platelet aggregation assessed with light transmission aggregometry (20 µM adenosine diphosphate) ranged from 84% to 89% from 15 through 60 minutes after the 20 µg/kg bolus and from 92% to 95% after the 25 µg/kg bolus of tirofiban (see Table 1).

TABLE 1

% Inhibition of platelet aggregation 15–60 minutes after bolus injection

| 10 µg/kg | 20 µg/kg | 25 µg/kg |
| --- | --- | --- |
| 61–66% | 84–89% | 92–95% |

The antiplatelet effects of the 20 and 25 µg/kg bolus were evaluated also by flow cytometric determination of the capacity to bind fibrinogen in response to 1 µM adenosine diphosphate. The extent of inhibition was greater after onset of treatment with the high bolus dose.

Light transmission aggregometry and rapid platelet function analyzer were performed with D-Phe-Pro-Arg-chloromethyl ketone as the anticoagulant and flow cytometry was performed with blood anticoagulated with corn trypsin inhibitor. Citrate and other chelators of calcium alter platelet reactivity and the inhibitory properties of GP IIb-IIIa inhibitors (Rebello et al., J. Thromb. Thrombolysis (2000) vol 9 pp. 23–28; Schneider et al. Circulation (1997) vol. 96 pp. 2877–83). Accordingly, the evlauations were performed with conditions that limit potentially confounding influences of selected anticoagulants and simulate intense exposure of platelets to multiple platelet agonists during thrombosis by using high concentrations of adenosine diphosphate and thrombin receptor agonist peptide.

The interval from 15 to 60 minutes after onset of treatment is a critical period during which iatrogenic vessel injury is induced and a thrombogenic object (intra-coronary stent) is frequently introduced. The present invention identifies a dosage range of tirofiban hydrochloride that achieves an average inhibition of platelet aggregation of greater than 90% throughout the first hour after treatment. This dosage entails an increase in the bolus amount as compared to conventional bolus amounts (from 10 to 25 µg/kg), but no change in the rate or duration of the infusion.

EXAMPLE 2

Intravenous Formulations

An intravenous dosage form of (2-S-(n-Butylsulfonylamino)-3[4-(piperidin-4-yl)butyloxyphenyl] propionic acid hydrochloride (Active I) is prepared as follows:

| | |
| --- | --- |
| Active I | 0.5–10.0 mg |
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, Active I is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994).

EXAMPLE 3

Intravenous Formulations

A pharmaceutical composition was prepared at room temperature using Active I, a citrate buffer, and sodium chloride, to obtain a concentration of 0.25 mg/ml.

800 grams of water was introduced into a standard pharmaceutical mixing vessel. 0.25 grams of Active I was dissolved in the water. 2.7 grams sodium citrate and 0.16 grams citric acid were added to obtain a finished citrate concentration of 10 mM. 8 grams of sodium chloride was added. 200 grams of water was then added to achieve the desired final concentrations of ingredients. The resulting aqueous formulation had the following concentrations:

| Ingredient | Amount |
| --- | --- |
| Active I | 0.25 mg/ml |
| citrate buffer | 10 mM |
| sodium chloride | 8 mg/ml |

The finished concentrated formulation is stored in a standard USP Type I borosilicate glass container at 30–40 degrees C. Prior to compound administration, the concentrated formulation is diluted in a 4:1 ratio resulting in a finished concentration of 0.05 mg/ml and transferred to an infusion bag.

What is claimed is:

1. A method for inhibiting platelet aggregation in a patient in need thereof, comprising 1) administering to the patient a bolus injection of an active drug, in an amount of about 25 µg/kg, and 2) administering to the patient, after the bolus injection, an intravenous infusion for a period of between about 12 hours and about 72 hours, of the active drug, in an amount of about 0.15 µg/kg/min, wherein the active drug is tirofiban or a salt thereof.

2. A method of claim 1, wherein the salt is tirofiban hydrochloride.

3. A method of claim 2, wherein the amount of tirofiban hydrochloride in the bolus injection is 25 μg/kg.

4. A method of claim 3 wherein the intravenous infusion is between 12 hours and 72 hours.

5. A method of claim 4 wherein the intravenous infusion is between 18 hours and 72 hours.

6. A method for reducing the risk of acute coronary syndrome in a patient at risk to acute coronary syndrome, comprising 1) administering to the patient a bolus injection of an active drug, in an amount of about 25 μg/kg, and 2) administering to the patient, after the bolus injection, an intravenous infusion for a period of between about 12 hours and about 72 hours, of the active drug, in an amount of about 0.15 μg/kg/min, wherein the active drug is tirofiban or a salt thereof.

* * * * *